United States Patent [19]

Anderson et al.

[11] Patent Number: 5,241,960
[45] Date of Patent: Sep. 7, 1993

[54] DEFIBRILLATOR PULSE GENERATOR

[75] Inventors: Kenneth M. Anderson, Bloomington; Theodore P. Adams, Edina; Mark W. Kroll, Minnetonka, all of Minn.

[73] Assignee: Angeion Corporation, Plymouth, Minn.

[21] Appl. No.: 910,611

[22] Filed: Jul. 8, 1992

[51] Int. Cl.⁵ .............................................. A61N 1/39
[52] U.S. Cl. ...................................................... 607/5
[58] Field of Search ............ 128/419 P, 419 D, 419 R

[56] References Cited

U.S. PATENT DOCUMENTS

| 5,131,388 | 7/1992 | Pless et al. | 128/419 D |
| 5,133,353 | 7/1992 | Hauser | 128/419 D |
| 5,144,946 | 9/1992 | Weinberg et al. | 128/419 P |

OTHER PUBLICATIONS

Cardiac Pacemaker, Inc., St. Paul, MN; Model 1700; photocopy of product.
Ventritex, Sunnyvale, CA.; "Cadence" tiered therapy defibrillator Model V-100; photocopy of product.
Cardiac Pacemakers, Inc., St. Paul, MN; Ventak AICD, cardioverter defibrillator Models 1500, 1510, 1520; photocopy of product.
Medtronic, Inc., "Tachyarrhythmia Management", 1991, Annual Report 1991, pp. 12, 13.
Telectronics Pacing Systems, Inc., "Gaurdain ATP", 1990, Product Brochure, p. 1.
Cardiac Pacemakers, Inc., "Advanced AICD Therapy Made Easy", 1991, Product Brochure, pp. 1, 2.
Hook et al., Advances in Third-Generation ICD Therapy, Cardio, Nov. 1991 pp. 66-72.
Hammel et al., Implantation of a Cardioverter/Defibrillator in Subpectoral Region Combined with a Non-thoracotomy Lead System, Pace, vol. 15, Apr. 1992, pp. 367-368.

Primary Examiner—Kyle L. Howell
Assistant Examiner—George Manuel
Attorney, Agent, or Firm—Anthony G. Eggink

[57] ABSTRACT

A defibrillator pulse generator device for implantation in the pectoral position of a patient. The pulse generator device has a compact, light weight housing structure. A power source, a capacitive member and a sensing and control structure are enclosed in the housing structure. A connecting structure mounted on the housing provides connection to the electrode leads of the defibrillator system.

18 Claims, 5 Drawing Sheets

| | Capac-itor | Volts | Tilt | E std | Ideal E del | I pec |
|---|---|---|---|---|---|---|
| PRESENT DEVICE | 85uF | 750 | 60% | 24J | 20J | 5.67 A |
| PRIOR ART | 140uF | 643 | 70% | 29J | 26J | 5.67 A |

FIG. 10

DEFIBRILLATOR PULSE GENERATOR

BACKGROUND OF THE INVENTION

This invention relates to an automatic, implantable defibrillator pulse generator and particularly to a pulse generator device implantable in the pectoral position of a patient.

Prior art pulse generator devices for defibrillator systems are primarily directed to those placed in the abdominal cavity. Although pulse generator devices that permit pectoral implantation provide numerous advantages for implantable defibrillator systems, it has been difficult to develop a practical pulse generator device capable of being implanted in the pectoral position.

Present pulse generator devices implanted in the abdominal cavity are limited in function and have structures and configurations that may preclude implantation in the pectoral position for patient comfort and cosmetic purposes. Pulse generator devices constructed and arranged for pectoral implantation are provided in this invention.

SUMMARY OF THE INVENTION

An automatic defibrillator pulse generator device constructed and arranged for pectoral implantation. The pulse generator device has a compact, lightweight housing structure enclosing power means, capacitive means, and sensing and control means.

The pulse generator housing provides a cooperating structure, configuration and composition, and has a top connector portion with connecting ports in communication with the sensing and control means and for connection to the electrode leads of the defibrillator system.

The defibrillator pulse generator of this invention provides a device which utilizes a smaller capacitor and batteries than those of prior art devices and thus yields a pulse generator device which is capable of pectoral implantation. Although the compact pulse generator of this invention and its associated components are smaller and delivers a smaller shock to the heart, the pectoral implantation provides a better vector and more effective shock pulse width to yield an effective implantable defibrillator pulse generator.

These and other benefits of this invention will become clear from the following description by reference to the drawings.

BRIEF DESCRIPTION OF THE DRAWING FIGURES

FIGS. 8-10 are voltage versus time graphs and a comparison table, respectively, which show the defibrillation energy discharged from the capacitor used in the pulse generator of the present invention.

DESCRIPTION OF THE PREFERRED EMBODIMENTS

Figure 1:
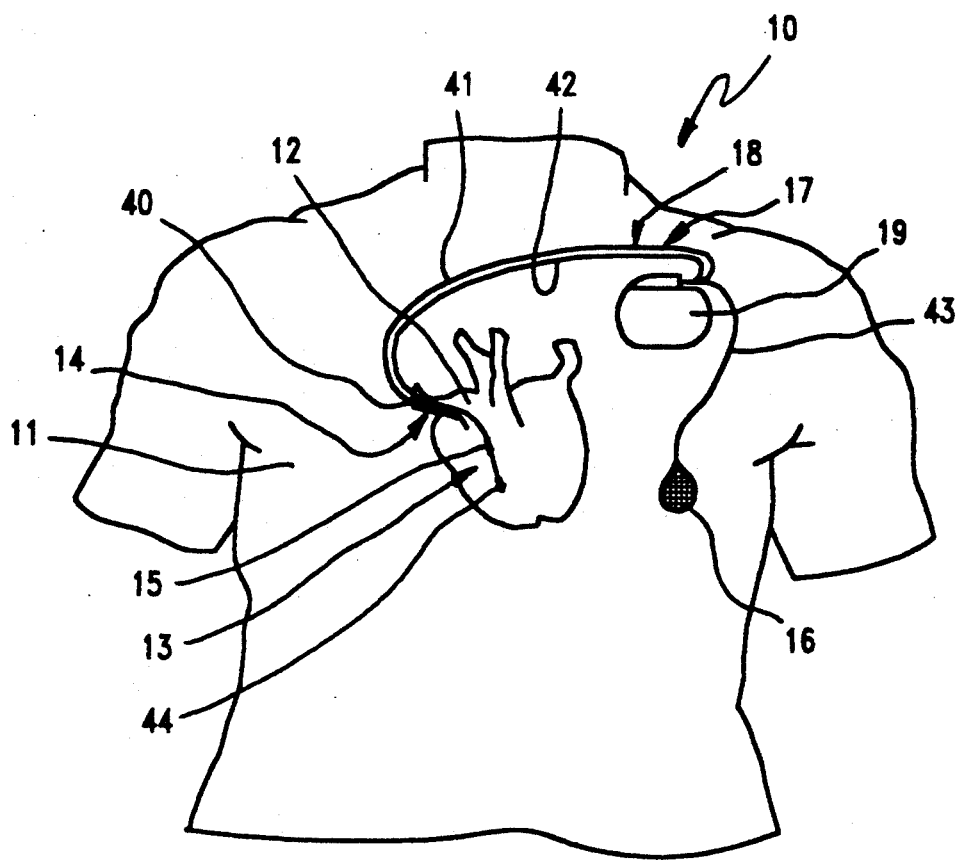
FIG. 1 is a frontal plan view showing the automatic, implantable defibrillator pulse generator device of this invention implanted in the pectoral position of a patient.

FIG. 1 shows the automatic defibrillator pulse generator 17 of the present invention implanted in the pectoral region 18 of the chest 11 of patient 10. The pulse generator 17 has a plurality of ports for connection to various implantable catheter and other electrode means, as is known in the art. For example, electrode leads 41 and 42 are shown extending from the pulse generator 17 to catheter electrodes 40 and 15 which are passed, respectively, into the superior venecava 14 and the right ventricle 13 of heart 12. Further, lead 43 is shown extending from the pulse generator 17 to a subcutaneous patch electrode 16. The specific configuration of the defibrillation system is dependent upon the requirements of the patient as determined by the physician.

Figures 2, 3:
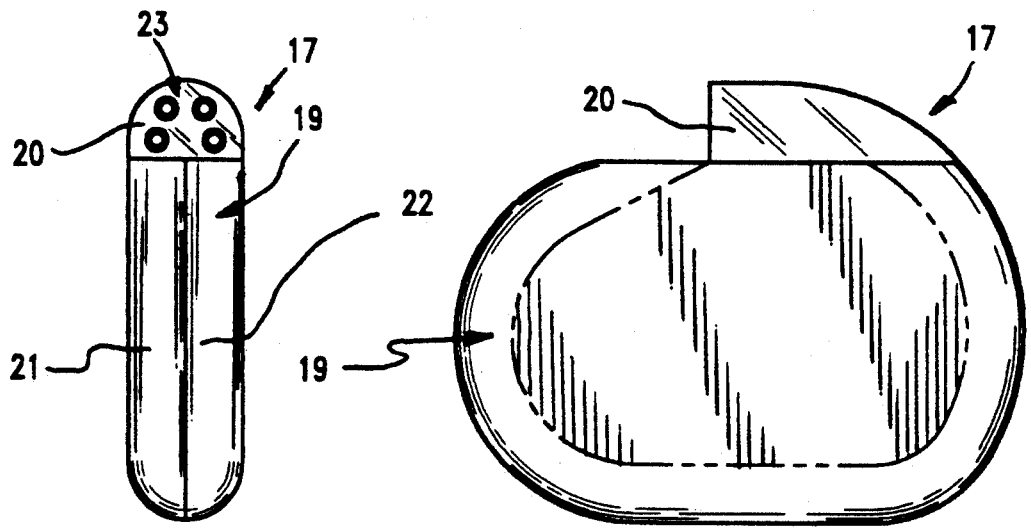
FIGS. 2 and 3 are frontal and side plan views, respectively, of the pulse generator device.

FIGS. 2 and 3 show the defibrillator pulse generator 17 comprised of a housing 19 having mating half shells 21 and 22. Positioned and mounted on top of housing 19 is a top connector portion 20 having a plurality of connecting ports 23 which are described further below. Importantly, the pulse generator 17 is comprised of a compact, self contained structure having predetermined dimensions which permits pectoral implantation. The housing 19 and top connector 20 are constructed and arranged to yield a cooperating structure which houses power means, control means and capacitive means. This cooperating structure permits pectoral implantation and provides a compact and effective pulse generator that automatically senses the bioelectrical signals of the heart and which is able to provide a 750 volt capacitive discharge, for example, to the heart for defibrillation purposes.

In the past, defibrillator pulse generators have required a size and configuration for functional purposes that necessitated implantation in the abdominal cavity of a patient. Such implantation has resulted in patient discomfort. However, the physical parameters of these prior art devices have prevented pectoral implantation, which is preferred by physicians and patients alike. Table 1 below shows the size and weight comparisons between known prior art devices and the defibrillator pulse generator 17 of the present invention.

TABLE 1

|  | Prior Art Devices % of total (by volume) | Present Device % of total (by volume) | Present Device % of Prior Art Devices (by volume) | Present Device % of Prior Art Devices (by weight) |
| --- | --- | --- | --- | --- |
| Connector | 10 | 8 | 30 | 32 |
| Capacitors | 30 | 38 | 63 | 62 |
| Batteries | 30 | 23 | 38 | 57 |
| Electronics | 30 | 31 | 50 | 43 |
| Total | 100% (120 CC) | 100% (60 CC) | 50% | 55% |

As shown in Table 1, the defibrillator pulse generator 17 of this invention, provides a pulse generator structure which is 50% of the volume of prior art devices and which has a weight which is 55% of the weight of the prior art devices. The connector means, capacitor means, power means and electronic means of the pulse generator 17 of the present invention are further described below.

It is important in this invention that the defibrillator pulse generator 17 be constructed and arranged for pectoral implantation. The housing structure 19 is a compact and lightweight structure made of a biocompatable material and has a contoured configuration. The overall structure of this invention has a weight of less than 150 grams, preferably less than 130 grams, and a volume of less than 60 cc. As shown in Table 1, the pulse generator 17 of this invention has generally 55% of the weight of prior art devices and a volume which is generally 50% of that of prior art devices. Table 1 further shows the weights and volumes of the respective components of this invention (connector, capacitor, batteries and electronics) as a percentage in weight and volume of the total and in comparison to prior art devices.

As further shown in FIGS. 2 and 3, the housing structure 19 has a contoured periphery which is matingly connected to the top connector member 20 which also has a mating contoured configuration. The housing 19 is constructed of a biocompatable material such as titanium or a stainless steel alloy. The top connector member 20 is also constructed of a biocompatable material, such as a biocompatible polymeric composition. It has further been found that for pectoral implantation purposes, that the housing structure 19 have a desired length to width to thickness ratio of approximately 5 to 3 to 1.

The capacitor, having a capacitance of approximately 85 $\mu$F, is constructed and arranged to deliver an initial 750 volt discharge and a effective energy pulse which is described below. The capacitor is in communication with the electronic circuitry output portion which generally is comprised of a flash type circuit which delivers the capacitor discharge through electrodes 15, 16 and 40, for example.

Figure 5:
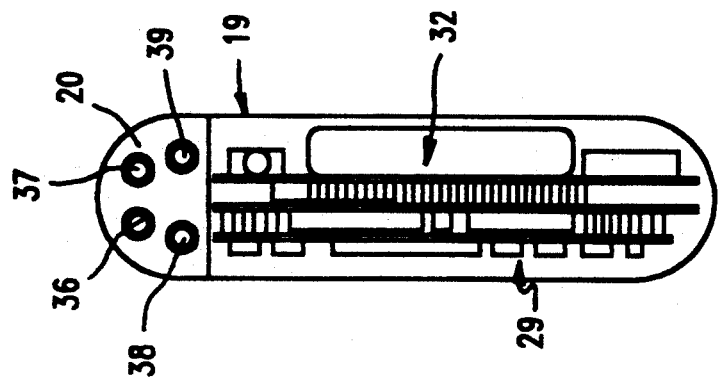
FIGS. 4 and 5 are side and frontal plan views, respectively, showing the power, capacitive, control and connecting means positioned in the pulse generator device.
Figure 4:
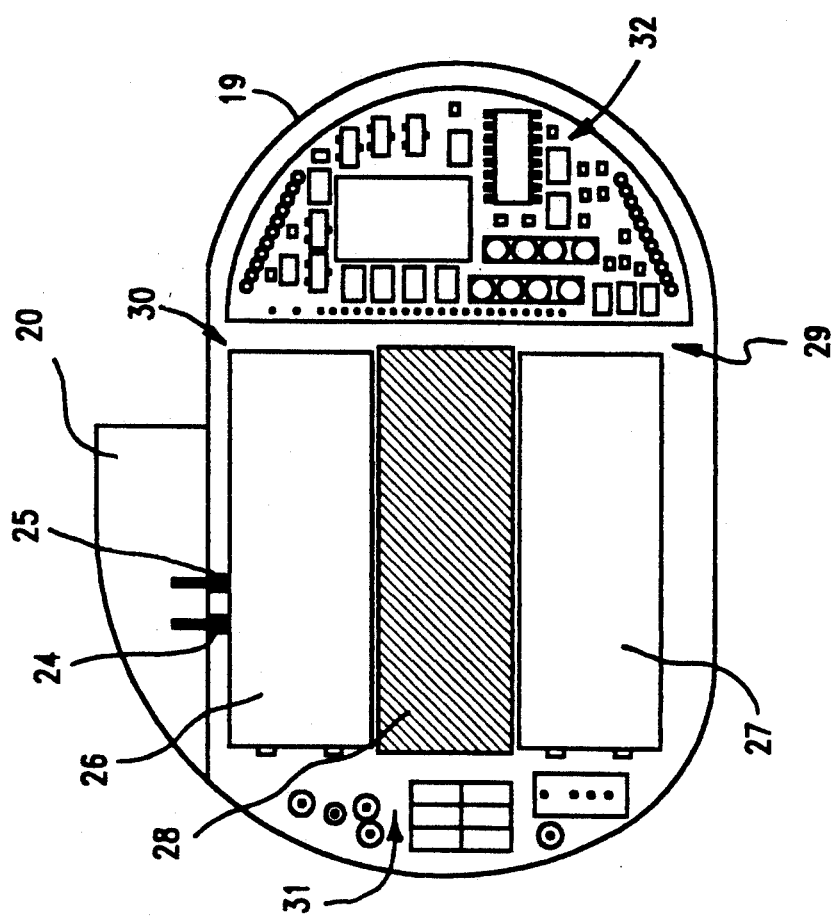

FIGS. 4 and 5 show the cannister housing 19 having an interior space 30 wherein batteries 26 and 27 are positioned and wherein the capacitor 28 and circuit board portions 31 and 32 are positioned. The top connector 20 is shown mounted to the top of the cannister housing 19. Connecting ports 36, 37, 38 and 39 are shown positioned in the top connector 20. The connecting ports 36 and 37 are connectible to the positive defibrillating electrode, for example, while connecting port 38 is connectible to the negative defibrillating electrode, for example, and the connecting port 39 receives the pacing/sensing lead. Channels 24 and 25 provide communicative and fastener members that provide for the attachment of the top connector 20 to the cannister housing 19 and for the electrical connection between the ports 36, 37, 38 and 39 and the electronic elements positioned in the interior space 30 of housing 19.

As discussed, the top connector 20 of the defibrillator pulse generator 17 has, for example, connecting ports 36(DF+), 37(DF+), 38(DF−) and 39 (sensing/pacing). The lead connected to the DF− port, for example, is in conductive contact with the catheter electrode 15 placed in the right ventricle 13 of the heart 12. The lead(s) connected to the DF+ port(s) are connected to either or both the electrode positioned in the superior venecava 14 and the subcutaneous patch electrode 16. Alternatively, the DF+ port holes may not be utilized, and plugged by a stopper means, for example, when the pulse generator body itself is utilized as the positive element to complete the defibrillation circuit. The pacing/sensing electrode 44 provides an input to connecting port 39 of the pulse generator 17 and provides continual monitoring of the pace of the heart. The circuitry of the pulse generator 17 has means to detect any tachycardiac condition and to thereby respond by the discharge of electrical energy.

The defibrillator pulse generator 17 of this invention provides a device which utilizes a smaller capacitor and batteries than those of prior art devices and thus yields a pulse generator device which is capable of pectoral implantation. Although the smaller unit and associated components are smaller and deliver a smaller shock to the heart, the pectoral implantation provides a better vector and more effective shock pulse width to yield an effective implantable defibrillator pulse generator.

Figure 6:
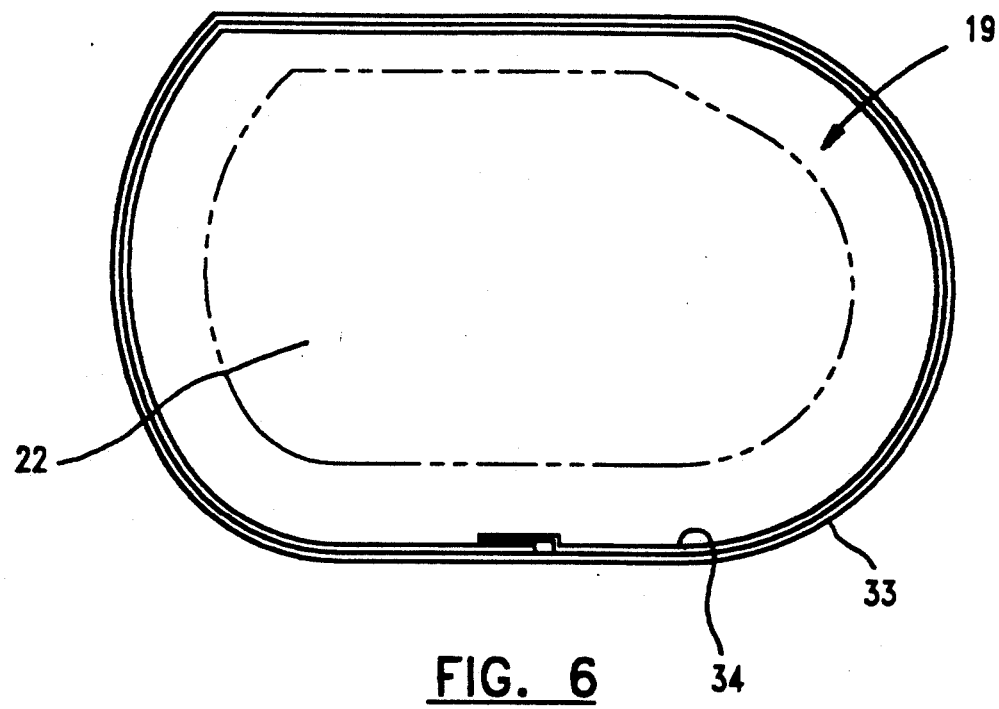
FIGS. 6 and 7 are plan views, showing the interior of the pulse generator housing structure.
Figure 7:
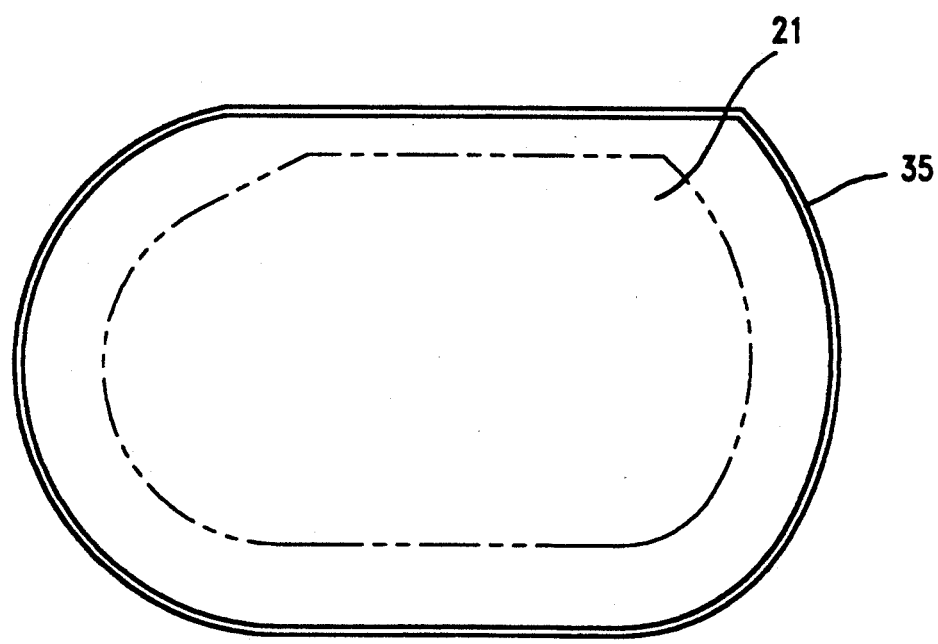

FIGS. 6 and 7 show the mating housing half shells 21 and 22, respectively of cannister housing 19. The half shell 22 is shown to have an interior peripheral band 34 which is fixed adjacent the peripheral edge 33. The interior peripheral band 34 extends outwardly from the edge 33 of half shell 22 and is constructed and arranged to receive the peripheral edge 35 of housing half shell 21. Alternatively, the peripheral band 34 may be mounted within housing half shell 21, whereby the half shell 22 is positioned thereabout. The peripheral band 34 is also provided to shield the electronic components within housing 19 during the welding process uniting the body shells 21 and 22.

The flexible circuit board 29 is mounted within the interior space 30 of housing 19. The circuit board 29 provides for the sensing/pacing circuitry in communication with the lead extending from connecting port 39, for example. When a fibrillation episode is detected, the circuit board 29 causes the capacitor 28 to discharge an initial 750 volt charge through the leads connected to ports 36–38, for example, and to the heart 12 of the patient 10. The electronic circuitry has a sensing portion which monitors the heart beat rate and which senses heart rate irregularity by means of two small electrodes 44, as is known in the art. The circuitry further has a processor portion which determines, with respect to a predetermined standard, when the output portion of the circuit will be activated.

Figure 8:
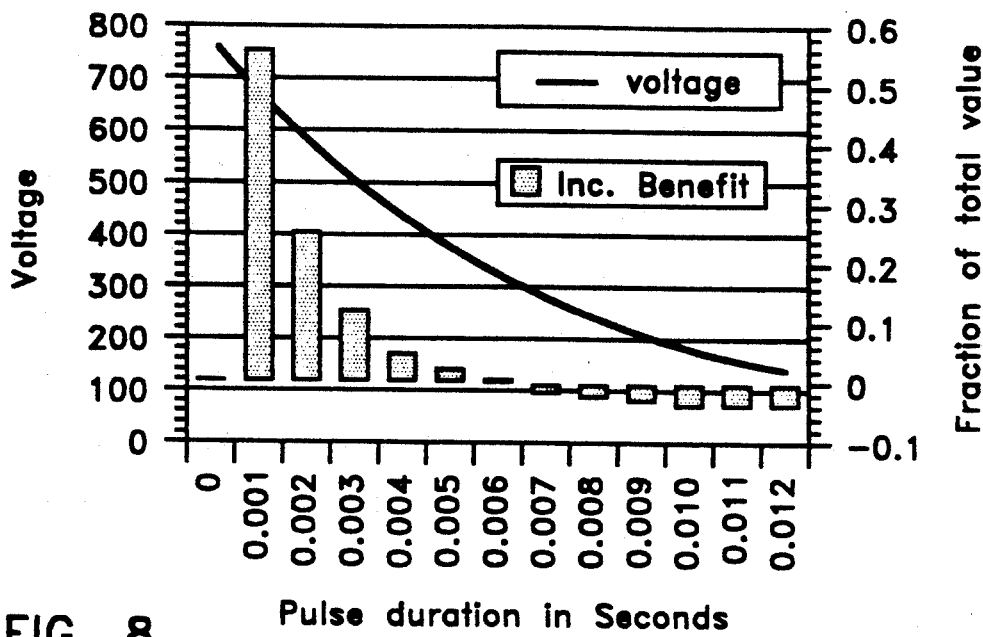
Figure 9:
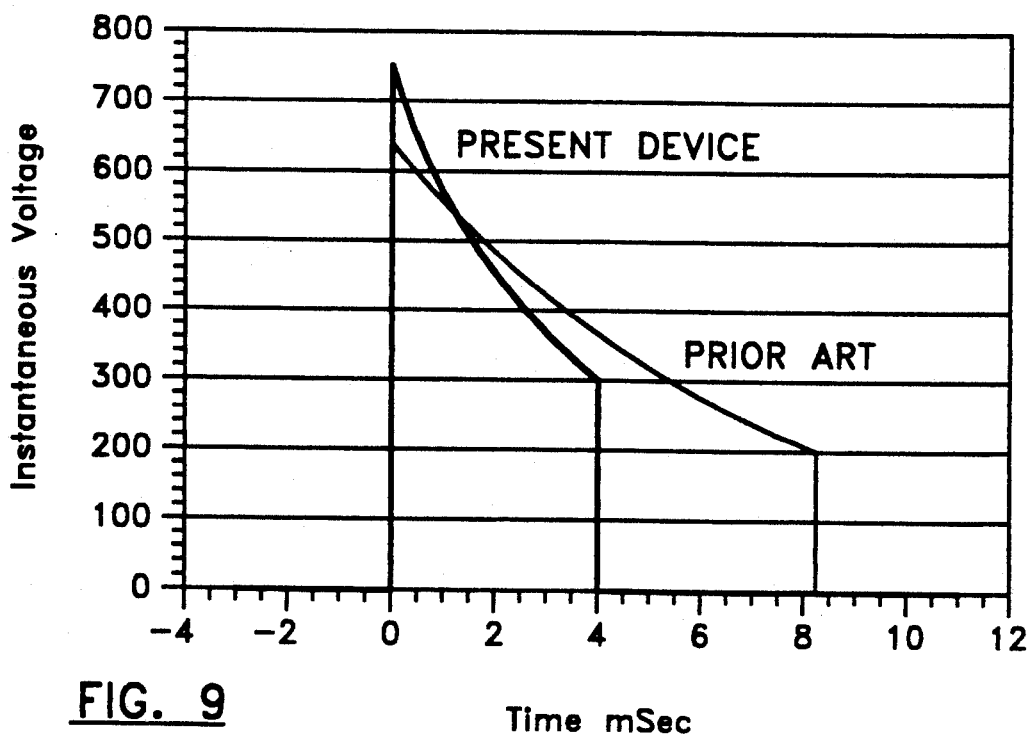

FIG. 8 is a graph showing the voltage discharge with respect to time from a 140 $\mu$F capacitor used in a prior art defibrillator pulse generator. As shown, no benefit is achieved after 0.006 seconds of shock delivery. The graph further shows incremental benefit of the voltage discharge with respect to time. FIG. 9 is a graph which shows the instantaneous voltage with respect to time (mSec.) and compares the plotted values of the 20 joule pulse with a 26 joule pulse generated from a prior art device. As shown, the defibrillator pulse generator of this invention truncates voltage delivery at 4 mSec. As summarized in the table of FIG. 10, the 85 $\mu$F capacitor of this invention delivers 20 joules of energy with an initial voltage of 750 volts. The 140 $\mu$F capacitor used in a prior art device delivers 26 joules of energy with an initial voltage of approximately 643 volts. As shown in FIG. 9, although the prior art device (140 $\mu$F capacitor) delivers a greater energy pulse than that of the 85 $\mu$F capacitor, the incremental benefit for defibrillation purposes as shown in FIG. 8 is diminished. Thus, the 85 $\mu$F capacitor utilized in the defibrillator pulse generator of the present invention provides an unexpected result and permits the smaller capacitor to be utilized in a compact housing 19 which has a size and weight that permits pectoral implantation.

As many changes are possible to the embodiments of this invention utilizing the teachings thereof, the descriptions above, and the accompanying drawings should be interpreted in the illustrative and not the limited sense.

That which is claimed is:

1. An automatic defibrillator pulse generator for pectoral implantation in a patient comprising:
   a) ergonomic enclosure means having connector means and further comprising a sealed housing structure constructed and arranged of a biocompatable material and having a volume of less than 60 cc and a weight of less than 150 grams; and
   b) capacitance means, power means, and sensing and control means contained in said enclosure means and being in communication with said connector means, said capacitance means having a capacitance value of approximately 85 µF, said pulse generator further being constructed and arranged to deliver approximately in initial 750 volt electrical charge and causing said capacitor to discharge for approximately 4 mSec. to the heart of a patient.

2. A defibrillator pulse generator for pectoral implantation comprising:
   a) a compact, lightweight biocompatable housing structure having a top connector member constructed of a biocompatable polymeric material and having at least one connecting port, said pulse generator having a weight of less than 150 grams;
   b) said housing being comprised of two unitable half shells having an interior peripheral band and having an interior volume of less than 60 cc. enclosing power means, capacitive means and control means; and
   c) said connecting port in said top connector member being communicatively connected to said power means, capacitive means and said control means, said capacitive means having a capacitance of approximately 85 µF and being constructed and arranged to deliver an initial charge of approximately 750 volts.

3. The defibrillator pulse generator of claim 2, wherein said housing has a contoured periphery.

4. The defibrillator pulse generator of claim 3, wherein said top connector member is constructed and arranged in a configuration contoured with said housing periphery contour.

5. The defibrillator pulse generator of claim 2, wherein said capacitive means has a specified volume which ranges between 40–80% of said housing interior volume.

6. The defibrillator pulse generator of claim 2, wherein said housing has a length to width to thickness ratio of approximately 5 to 3 to 1.

7. The defibrillator pulse generator of claim 2, wherein said power means is comprised of a battery, and said control means is comprised of a printed circuit board.

8. The defibrillator pulse generator of claim 2, wherein said biocompatable housing is metallic and comprised of a material selected from the group consisting of Titanium and a stainless steel alloy.

9. The defibrillator pulse generator of claim 2, wherein said housing is comprised of a metallic material having a biocompatable plastic coating.

10. The defibrillator pulse generator of claim 2, wherein said top connector member has four said connecting ports.

11. The defibrillator pulse generator of claim 2, wherein said control means includes sensing means and wherein said control means is comprised of a printed circuit board for mounting in said housing.

12. A small, lightweight housing for a defibrillator pulse generator for pectoral implantation in a patient, comprising a biocompatable housing containing power means, capacitive means having a capacitance value of approximately 85 µF for providing an effective and efficient defibrillation charge and sensing and control means and further having connector means fixed thereto, said pulse generator having a total weight of less than 150 grams and a volume of less than 60 cc.

13. The defibrillator pulse generator housing of claim 12, wherein said housing and connector means have contoured peripheries.

14. The defibrillator pulse generator housing of claim 12, wherein said biocompatable housing is metallic and comprised of two mating half shells and is further comprised of a material selected from the group consisting of Titanium and a stainless steel alloy.

15. The defibrillator pulse generator housing of claim 12, wherein said housing has a length to width to thickness ratio of approximately 5 to 3 to 1.

16. The defibrillator pulse generator housing of claim 12, wherein said connector means is comprised of a biocompatable plastic composition.

17. The defibrillator pulse generator housing of claim 12, wherein said power means is comprised of batteries.

18. The defibrillator pulse generator housing of claim 12, wherein said housing space contains a capacitor having a specified volume which ranges between 40 to 80% of the total housing volume.

* * * * *